United States Patent [19]
Bramberga et al.

[11] 3,955,559
[45] May 11, 1976

[54] METHOD OF CYTOLOGICAL DIAGNOSIS OF PRECANCER CONDITIONS AND CANCER

[76] Inventors: Velta Mikelevna Bramberga, ulitsa Gergora, 8, kv. 20; Arkady Yakovlevich Khesin, ulitsa Suvorova, 16, kv. 18; Teodor Arvidovich Grendze, ulitsa Suvorova, 16, kv. 24; Mark Naumovich Libenson, ulitsa Sverdlova, 7, kv. 2, all of Riga, U.S.S.R.

[22] Filed: Aug. 13, 1974

[21] Appl. No.: 496,996

[52] U.S. Cl. .............................. 128/2 R; 23/230 B
[51] Int. Cl.² ............................................. A61B 5/00
[58] Field of Search ................... 128/2 R, 2 B, 2 A; 23/230 B; 424/2, 3

[56] References Cited
UNITED STATES PATENTS

| | | |
|---|---|---|
| 3,315,229 | 4/1967 | Smithline ....................... 128/2 A X |
| 3,476,514 | 11/1969 | Roth ................................. 23/230 B |
| 3,515,516 | 6/1970 | Horton .............................. 424/3 X |
| 3,690,310 | 9/1972 | Mintz ................................ 128/2 R |
| 3,856,930 | 12/1974 | Nodine et al .................. 23/230 B X |

OTHER PUBLICATIONS

Excerpta Medica, Cancer, Sec. 16, Vol. 16, No. 12, Dec. 1968, Abstract No. 7119, p. 1126.

*Primary Examiner*—Kyle L. Howell
*Attorney, Agent, or Firm*—Holman & Stern

[57] ABSTRACT

The method for cytological diagnosis for precancer conditions and cancer which consists in the fact that the coefficient of the cell size is calculated for each cell in the cytological sample from the area of the nucleus, and the area of the cytoplasm, and where the values exceeding 0.5 are selected and used to determine the mean value which serves as a criterion for diagnosing the disease.

1 Claim, 3 Drawing Figures

METHOD OF CYTOLOGICAL DIAGNOSIS OF PRECANCER CONDITIONS AND CANCER

BACKGROUND OF THE INVENTION

The invention relates to medicine, and more particularly it relates to methods of cytological diagnosis for cancer and precancer conditions, and can therefore be used in medical practice, scientific research, and prophylaxis.

The proposed method can also be used for prophylactic examination of populations on a mass scale for early revealing oncological diseases.

The invention can be used for diagnosis of cells by their size taken from cytological material of the patient, such as biopsy material, washing waters, vaginal scrapes, exudate, and pathological secretion, which cells are fixed and stained by methods suitable for measuring areas of the nucleus and the cell. The cell area can be determined in micrometers, planimeters, etc., and also by various other modes.

Various measuring and computing apparati for the automation of cytological diagnosis of cancer and pre cancer conditions has evoked interest as to dimensional signs as the most promising criterion in the technical realization of diagnosing cytological preparations. On the one hand, it is common knowledge that malignant processes are characterized by the increased area of the cell nucleus. As far back as in 1952, Johnston proposed that the ratio of the cell nucleus to the cytoplasm should be used as a criterion for diagnosing cancer and precancer conditions. On the other hand, technical means have been developed that can be used to measure the linear dimensions of micro-object images, for example, by analyzing usually the image from a scanning electron microscope.

However, the practical measurement of areas of nuclei and cytoplasm in more than two thousand cells in normal, precancer, and cancer cytological preparations, and the subsequent analysis, have shown that the size of the area of the cell nucleus is a less important criterion for diagnosing cancer and precancer conditions compared with the ratio of the area of the nucleus to the area of the cytoplasm in the cell.

Methods for cytological diagnosis of cancer conditions are known in the prior art, which consist of measuring the following: the ratio of the nucleus area to the area of the cell; the optical density of the nucleus; and the DNA and RNA content of the cell. The known methods, however, have certain disadvantages, which are as follows: it is impossible to differentiate precancer and cancer conditions using only one sign as a criterion; the difficulties encountered by the Examiner in measuring the areas of the cells and their nuclei are not justified by the low trustworthiness of the diagnosis;
it is necessary to measure a great number of cells in the preparation, while some cytological preparations only contain insignificant quantities of pathologically modified cells (atypical cells) and cannot therefore be used for diagnostic purposes; and at the same time, the assessment of the other preparations require much additional time.

SUMMARY OF THE INVENTION

The object of the invention is therefore to provide a differential cytological diagnosis of cancer and precancer conditions with high degree of trustworthiness by using certain dimensional signs of the cell as criteria.

Another object of the invention is to provide differential cytological diagnosis of cancer and precancer conditions from cytological preparations containing small quantities of pathologically modified (atypical) cells.

These and other objects of the invention are attained by this novel technique according to which cytological preparations are taken from suspected patients, and the area of the nucleus and of the cytoplasm is measured in each examined cell. Next, according to the invention, the coefficient of the cell size is calculated for each cell; to that end, the ratio of said area of the nucleus to said area of the cytoplasm is first calculated; the value of the cell nucleus area is multiplied by the constant coefficient selected from the values ranging from 0 to 0.025, and said ratio of the nucleus area to the area of the cytoplasm is summed up with the value of the nucleus area multiplied by said calculated coefficient. Values not exceeding 0.5 are selected from the thus-obtained multitude of the coefficients of the cell size, and the mean value is found for the selected values. If the mean value of the cell size coefficients falls within 0.5–0.6, the preparation is diagnosed to belong to a healthy person; if the mean value is from 0.6 to 0.8., the preparation is considered to belong to a patient with a precancer condition, and finally, if the mean value of the cell size coefficient exceeds 0.8, the preparation should be considered as belonging to a patient with cancer.

BRIEF DESCRIPTION OF THE DRAWINGS

For a better understanding of the invention, the method for differential cytological diagnosis of cancer and precancer conditions is illustrated by a detailed description of practical examples of its embodiment, and the appended drawings in which.

DESCRIPTION OF THE PREFERRED EMBODIMENT

The essence of the proposed invention of cytological diagnosis of cancer and precancer consists in the following; cytological preparations are taken from the patients in whom precancer or cancer is suspected, by any known method.

Then, the area of the nucleus $S_1$ and the area of cytoplasm (i.e., of the whole cell) $S_2$ of each examined cell are measured in the selected cytological preparations. The known method can be used to measure two perpendicularly arranged diameters of the nucleus and two mutually perpendicular diameters of the cell with the aid of a micrometer. Areas of nuclei $S_1$ and of cytoplasm $S_2$ are determined from the known formulas of the area of an ellipse or the area of a circle.

Next, according to the invention, the coefficient of the cell size is determined for each cell under investigation, for which purpose the ratio of the area of the nucleus to the area of the cytoplasm is first determined from the formula $$\nu = (S_1/S_2)$$

where $\nu$ is the nucleus-to-cytoplasm ratio.

This value is quite characteristic of cells in cancer and precancer preparations, which is due to the increased growth of the nucleus with respect to the cytoplasm.

The ratio $\nu$ $(S_1/S_2)$ can be used as an independent criterion in diagnosing cancer and precancer preparations.

Figure 1:
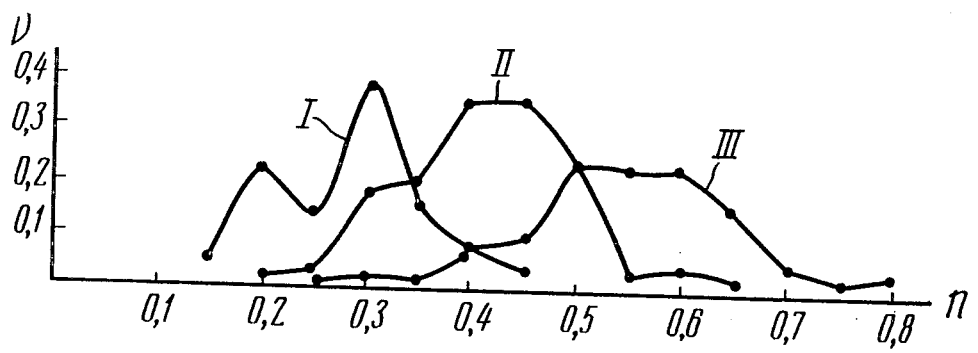
FIG. 1 shows a distribution of cells in cytological preparations: normal (I), precancer (II), and cancer (III), according to the ratio of the areas of the nuclei to the areas of their cells (nucleus-to-cytoplasm ratio) according to the invention.

In FIG. 1, the values of the nucleus-to-cytoplasm ratio '$\nu$' are plotted against the Y axis, and the relative quantities of the examined cells $n$ are plotted against the x axis. Curve I illustrates the distribution of normal preparation cells, for which the value of the nucleus-to-cytoplasm ratio "$\nu$" is high; curve II shows the distribution of cells for precancer preparations for which the value of the nucleus-to-cytoplasm ratio $\nu$ is medium in magnitude, and finally curve III shows the distribution of the cancer preparation cells which are characterized by low values of the nucleus-to-cytoplasm ratio.

It follows from the graph that curves I, II and III of the distribution of normal, precancer, and cancer cells of cytological preparations intersect, and in order to ensure reliable diagnosis it is necessary to examine a great number of cells.

The next step in the proposed method is the summation of the nucleus-to-cytoplasm ratio $\nu$ with the area of the nucleus S multiplied by the constant coefficient c, the value of which is selected within the range of 0 to 0.025.

The diagnostic sign, the coefficient $\eta$ (c) of the cell size can be expressed now in the form of the following formula;

$$\eta (c) = \nu + cS_1 = (S_1/S_2) + cS_1$$

where
$S_1$ is the area of the nucleus;
$S_2$ is the area of the cytoplsm;
$\nu$ is the nucleus-to-cytoplasm ratio;
$c$ is the constant coefficient.

Figure 2:
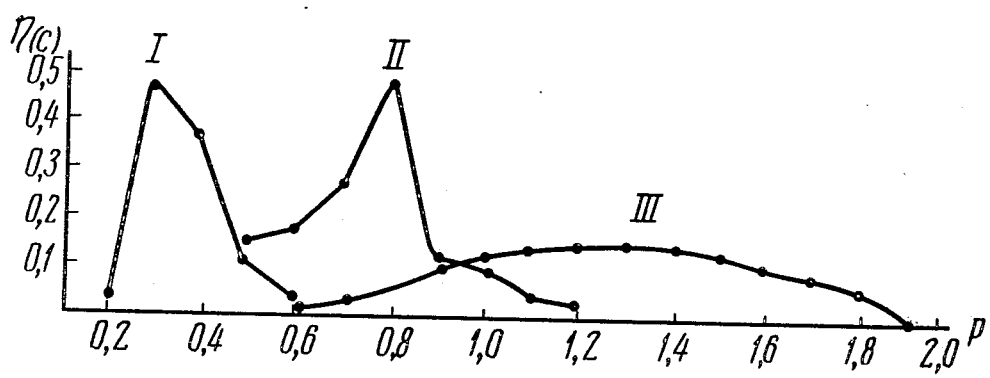
FIG. 2 is a distribution curve of normal cells (I), precancer cells (II) and cancer (III) cells in cytological preparations by the cell size coefficients according to the invention.

The significance of the coefficient $c$ in the above formula is in fact that unlike $\nu$, which is a dimensionless unit, the absolute value of $S_1$ varies with changing units of measurement. This is why, when the summary criterion is used, the area of the nucleus should be multiplied by the coefficient '$p$' the unit of which is reciprocal of that of the nucleus area $S_1$. Moreover, when using the summary criterion, it is necessary to remember that the diagnostic value of each component is different. (For example, it is known that the nucleus-to-cytoplasm ratio is a more valuable diagnostic component than the area of the nucleus). For this reason the area of the nucleus should also be multiplied by the weight coefficient '$\alpha$'. It appears, as a result, that $c=p\cdot\alpha$. In FIG. 2, the values of the coefficient $\eta$ $(c)$— of the size of cells of normal, precancer, and cancer preparations are plotted against the axis of ordinates, and their relative occurrence $p$ is plotted against the axis of abscissas. (Curve I characterizes the cells of normal cytological preparations, curve II - precancer, and curve III cells of cancer preparations).

The comparison of the curves in FIGS. 1 and 2, shows that the number of cells in the zone of intersection of curves I and II, and of curves II and III, is markedly less. The experiments have shown that the quantity of the cells in the zone of intersection of curves I and II decreases 2.5 times, and in the zone of intersection of curves II and III, 3.5 times.

The proposed method does not provide for additional measurements as is the case with measuring the area of the nucleus $S_1$ and of the cytoplasm $S_2$ in determining the nucleus-to-cytoplasm ratio.

Preliminarily calculated values of the constant coefficient $c$ (which is within the range from 0 to 0.025) are suitable for all precancer and cancer conditions; for any disease, the optimum value of the coefficient falls within this range.

Analysis and calculations made on the basis of the dimensional signs have shown that the law of distribution of the values of the cell size coefficient $\eta$ $(c)$ for cells of cancer and precancer preparations are rather close to the normal.

The measure of the quality of classification of atypical cells of cancer and precancer preparations is the value $$Z(c) = \frac{\mu_1(c) - \mu_2(c)}{\delta_1(c) + \delta_2(c)}$$

where
$\mu_1(c)$ is the mathematic expectation of cancer cells;
$\delta_1(c)$ is the root-mean-square error of cancer cells;
$\mu_2(c)$ is the mathematic expectation of precancer cells;
$\delta_2(c)$ is the root-mean-square error of precancer cells.

It is quite obvious that the higher the quality of classification, the greater the value Z(c).

Figure 3:
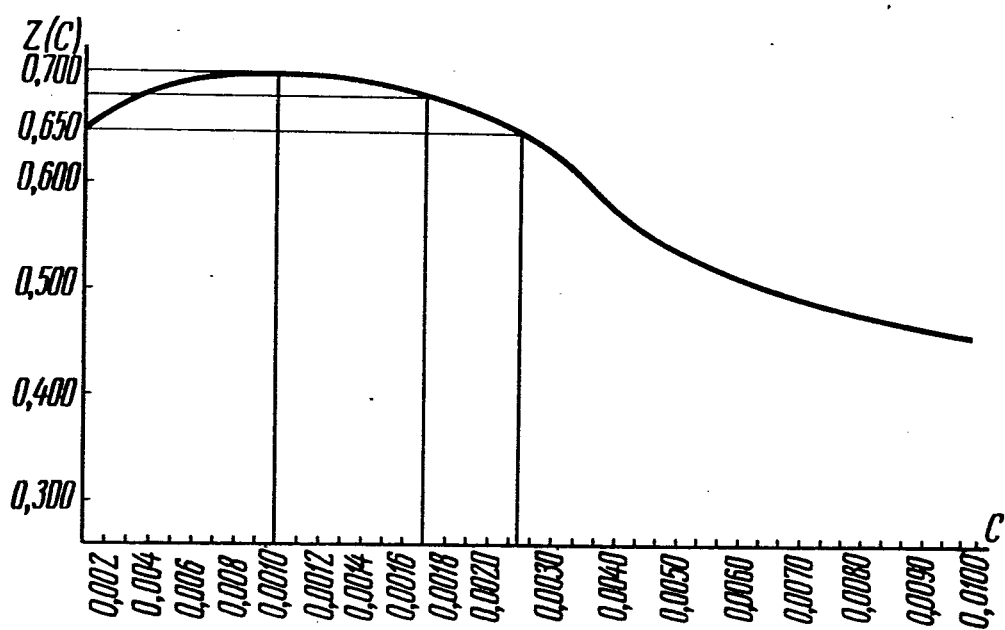
FIG. 3 is a curve illustrating the dependence of the quality of diagnosis of pathologically modified (atypical) cells of precancer and cancer cytological preparations on the constant coefficient of cell size, according to the invention.

In FIG. 3, the values of the constant coefficient $c$ are plotted against the axis of abscissas, and the assessment of the quality of the diagnosis (classification Z (c) according to sign $\eta$ (c) that is, the coefficient of the cell size) is plotted against the axis of ordinates. The range of values from 0 to 0.025 is the basis for selection of the constant coefficient $c$ for the diagnostic criterion of the cell size coefficient $\eta$ (c).

It follows from FIG. 3, that at C=0, the informative value of the cell size coefficient $\eta$ (c) is equal to the informative value of the nucleus-to-cytoplasm ratio $\nu$ in the differential cytological diagnosis. For example, the value C=0.010 for the localization of the "uterine cervix" is optimum for diagnosis with the aid of the cell size coefficient $\eta$ (c). The informative reliability of this coefficient falls from the value of C=0.010 to C=0.20.

Next, according to the invention, from the multitude of calculated values for the cell size coefficients $\eta$ (c), those exceeding 0.5 are selected. The mean value is calculated from the selected values, and if the mean value of the cell size coefficient $\eta$ (c) falls within the range of 0.5–0.6, the preparation is diagnosed as belonging to a healthy person; if the mean value of the cell size coefficient $\eta$ (c) is within the range of 0.6 – 0.8, the preparation is diagnosed to belong to a patient with a precancer condition, and if the mean value of the cell size coefficient $\eta$ (c) exceeds 0.8, the preparation is considered to belong to a patient with cancer.

In order to clarify the effectiveness of the diagnosis by the cell size coefficient $\eta$ (c) during cytological diagnosis of cancer and precancer from sufficiently representative selection of pathologically changed (atypical) cells selected according to some other signs, a range of optimum values for the constant coefficient C from 0.006 to 0.0017 was selected from preparations with verified diagnosis.

At the second step, the following values for the coefficient C were selected: $C_1 = 0.0017$, $C_2 = 0.0013$, $C_3 = 0.001$ and $C_o = 0$ (which corresponds to the value of the nucleus-to-cytoplasm ratio $\nu$ ). The processing of the results on a computer, for example, for cancer and precancer conditions of the uterine cervix, is provided for the following conclusions: the weight coefficient L lies within the range of 0.06–0.17. In order to ensure reliable diagnosis, it is sufficient to analyze twelve pathologically changed (atypical) cells. This is a comparatively small number, considering the practical diagnostic possibilities, and requiring relatively short time periods to perform.

The comparison of the nucleus-to-cytoplasm ratio $\nu$ and the cell size coefficient $\eta$ (c) against the criterion $Z(c)$ of the quality of the diagnosis, shows that with the number of examined cells 12 ($n = 12$), the cell size coefficient $\eta$ (c) provides for the results that are 2.5 times better.

From consideration of labor economy, the cell size coefficient $\eta$ (c) can be used to diagnose three cytological preparations instead of four, as is the case with the use of the nucleus-to-cytoplasm ratio alone.

The nucleus-to-cytoplasm ratio $\nu$ and the cell size coefficient $\eta$ (c) were determined for atypical cells in cytological preparations taken from patients with cancer and precancer of the stomach, lungs, and uterine cervix.

Cytological preparations were taken from operation and biopsy material, and washing waters from the stomach and bronchi. The preparations were also obtained from the vaginal secretion and scraped from lesions.

The preparations were stained by Leishmans' method with azure II - eosin and 3,400 cells taken from 55 patients were examined.

The atypical cells in the cytological preparations were measured under a microscope (eye-piece X7, and the lens X90). The diameters of the nuclei and cells were measured in two mutually perpendicular directions. The diameters were determined by counting the divisions in the micrometric eye-piece. From 30 to 100 cells were measured in each preparation.

Tables 1 and 2 represent the following: the quantity of patients examined, the number of examined cells, and the results obtained for various localization of tumours.

Table 1.

Assessment of mathematical expectation $\mu$ (c) and root-mean-square error $\delta$ (c) of the nucleus-to-cytoplasm ratio $\nu$ and the cell size coefficient $\eta$ (c) for the whole group of patients with cancer or precancer of stomach, lung, and uterine cervix.

Table 2.

Examples of values of mathematical expectation $\mu(c)$ and root-mean-square error $\delta$ (c) of the nucleus-to-cytoplasm ratio $\nu$ and the cell size coefficient $\eta$ (c) for individual patients with cancer and precancer of stomach, lungs and uterine cervix.

The symbol $\mu$ (c) is used to designate the mathematical expectation, and $\delta$ (c) to designate the root-means-square error.

Table 1

| Nos | Diagnosis | Record No. (Qty of patients examined) | Qty of cells | Nucleus-to-cytoplasm ratio $\mu$ : $\delta$ | | Cell size coefficient $\mu$ : $\delta$ | |
|---|---|---|---|---|---|---|---|
| 1. | Cancer of uterine cervix | 2, 3, 128, 132, 129 127, 135, 133, 142, 143, 145 | 150 | 0.494 | 0.112 | 0.681 | 0.137 |
| 2. | Precancer of uterine cervix | 139, 140, 136, 141, 137, 138, 7, 8, 9, 11 | 500 | 0.364 | 0.089 | 0.511 | 0.106 |
| 3. | Cancer of stomach | 26, 39, 27, 36, 29, 40, 38, 32, 28, 25 | 1000 | 0.657 | 0.092 | 0.848 | 0.130 |
| 4. | Precancer of stomach | 42, 48, 47, 49, 13, 45, 115, 11, 55, 54 | 1000 | 0.389 | 0.078 | 0.497 | 0.090 |
| 5. | Cancer of lungs | 16, 15, 14, 68, 34, 67, 88, 19, 18, 17 | 500 | 0.571 | 0.100 | 0.733 | 0.127 |
| 6. | Precancer of lungs | 24, 21, 20, 22, 23 | 250 | 0.421 | 0.063 | 0.531 | 0.069 |

| No. | Diagnosis | Record No. | Histological diagnosis | Material |
|---|---|---|---|---|
| 1. | Cancer of lungs | 67 | Flat-cell cancer with cornification | Smear from biopsy material |
| 2. | Cancer of lungs | 34 | Inadequate differentitation | Smear of broncheal washings |
| 3. | Chronic pneumonia | 24 | Chronic pneumonia | same |
| 4. | Chronic pneumonia | 20 | Chronic pneumonia | same |
| 5. | Cancer of stomach | 27 | Glandular cancer | Smear from operation material |
| 6. | Cancer of stomach | 39 | same | same |
| 7. | Chronic gastritis | 56 | absent | Smear of gastric washings |
| 8. | Chronic gastritis | 53 | absent | same |
| 9. | Cancer of cervix | 10 | Low-differentiated cancer | Scrapes from lesion |
| 10. | Cancer of cervix | 5 | Solid cancer | same |
| 11. | Cervical erosion | 11 | Granulated tissue | Scrapes from lesion |

Table 2

| Staining | Nucleus-to-cytoplasm ratio | | Cell size coefficient | |
|---|---|---|---|---|
| | $\mu$ | $\delta$ | $\mu$ | $\delta$ |
| Leishman (azure II - cosin) | 0.578 | 0.100 | 0.738 | 0.108 |
| | 0.529 | 0.136 | 0.764 | 0.112 |
| | 0.429 | 0.057 | 0.541 | 0.065 |
| | 0.434 | 0.075 | 0.542 | 0.080 |
| | 0.677 | 0.076 | 0.885 | 0.130 |
| | 0.708 | 0.098 | 0.890 | 0.141 |
| | 0.390 | 0.121 | 0.490 | 0.131 |
| | 0.371 | 0.089 | 0.484 | 0.098 |
| | 0.500 | 0.112 | 0.718 | 0.130 |
| | 0.558 | 0.104 | 0.687 | 0.126 |
| | 0.312 | 0.104 | 0.450 | 0.112 |

What we claim is:

1. A method for the cytological diagnosis of cancer and precancer conditions, comprising taking a cytological preparation from a suspected patient; measuring the area of the nucleus and the area of the cytoplasm in each cell under examination; determining the coefficient of the cell size $\eta(c)$ for each said cell according to the relationship $$\eta(c) = \nu + cS_1 = (S_1/S_2) + cS_1$$

where
 $\nu$ = the nucleus to cytoplasm ratio
 $S_1$ = the area of the nucleus
 $S_2$ = the area of the cytoplasm
 $C$ = a constant coefficient of from 0 to 0.025;
selecting from the thus obtained multitude of cell size coefficients, the values exceeding 0.5; and determining the mean value for the selected values of the cell size coefficients, whereby if said mean value of the cell size coefficient falls within the range of from 0.0 to 0.6, the preparation is considered to belong to a healthy person; if the mean value of the cell size coefficient is from 0.6 to 0.8, the preparation is considered to belong to a patient with a precancer condition; and, finally, if the mean value of the cell size coefficient exceeds 0.9, the preparation is diagnosed as belonging to a patient with cancer.

* * * * *